United States Patent
Whalen et al.

(10) Patent No.: US 11,302,434 B2
(45) Date of Patent: Apr. 12, 2022

(54) NUTRITION-BASED MANAGEMENT OF HEALTH CONDITIONS USING MACHINE LEARNING

(71) Applicant: International Business Machines Corporation, Armonk, NY (US)

(72) Inventors: Diane Whalen, Franklin, MA (US); Fang Lu, Billerica, MA (US)

(73) Assignee: International Business Machines Corporation, Armonk, NY (US)

(*) Notice: Subject to any disclaimer, the term of this patent is extended or adjusted under 35 U.S.C. 154(b) by 293 days.

(21) Appl. No.: 16/558,650

(22) Filed: Sep. 3, 2019

(65) Prior Publication Data

US 2021/0065872 A1   Mar. 4, 2021

(51) Int. Cl.
*G16H 20/60* (2018.01)
*G06N 20/00* (2019.01)
(Continued)

(52) U.S. Cl.
CPC ........... *G16H 20/60* (2018.01); *G06N 20/00* (2019.01); *G16H 20/10* (2018.01)

(58) Field of Classification Search
None
See application file for complete search history.

(56) References Cited

U.S. PATENT DOCUMENTS

| 10,231,622 B2 | 3/2019 | Soyao et al. | |
| 2009/0004168 A1* | 1/2009 | Schakel | A61K 36/74 424/94.1 |

(Continued)

FOREIGN PATENT DOCUMENTS

| WO | WO-2017223192 A1 * | 12/2017 | ............. G06N 7/005 |
| WO | WO-2019144116 A1 * | 7/2019 | ............. G16H 40/20 |

OTHER PUBLICATIONS

Anonymous, Method and Apparatus for Improved Patient Management, IP.com Prior Art Database Technical Disclosure, Publication Date Oct. 18, 2007, pp. 1-4.
(Continued)

*Primary Examiner* — Evangeline Barr
*Assistant Examiner* — Tatyana N Grant
(74) *Attorney, Agent, or Firm* — Edell, Shapiro & Finnan, LLC

(57) ABSTRACT

A computer system provides nutrition-based management of health conditions using machine learning. Health information of a user is evaluated to determine a health condition. Medication information for the user is analyzed and the medication information is mapped to the health condition. One or more natural treatments for the user are determined from information sources based on the mapped health condition and medication information, wherein the one or more natural treatments include one or more from a group of nutrition and mind/body treatments, and wherein the information sources include information from crowdsourcing. The one or more natural treatments and medication information for the health condition are indicated. Embodiments of the present invention further include a method and program product for providing nutrition-based management of health conditions using machine learning in substantially the same manner described above.

15 Claims, 4 Drawing Sheets

(51) Int. Cl.
*G16H 20/10* (2018.01)
*G16H 10/20* (2018.01)
*G16H 40/67* (2018.01)
*G16H 50/20* (2018.01)

(56) References Cited

U.S. PATENT DOCUMENTS

| | | | |
|---|---|---|---|
| 2011/0166881 A1* | 7/2011 | Brazzo | G06Q 30/02 705/3 |
| 2012/0089617 A1* | 4/2012 | Frey | G06F 16/951 707/748 |
| 2012/0245952 A1* | 9/2012 | Halterman | G16H 50/20 705/2 |
| 2014/0019151 A1 | 1/2014 | Adami et al. | |
| 2014/0221785 A1 | 8/2014 | Pacione et al. | |
| 2016/0235362 A1* | 8/2016 | Lin | A61B 5/4854 |
| 2018/0196921 A1* | 7/2018 | Devarakonda | G16H 50/70 |
| 2018/0240359 A1* | 8/2018 | Hujsak | G06N 5/022 |
| 2020/0251213 A1* | 8/2020 | Tran | G16H 50/70 |

OTHER PUBLICATIONS

Anonymous, Medical Diagnostic and Treatment Module for Advanced Patient Management, IP.com Prior Art Database Technical Disclosure, Publication Date Feb. 27, 2008, pp. 1-10.

Anonymous, Holistic, Policy-Driven, Access Control for Smarter Healthcare, IP.com Prior Art Database Technical Disclosure, Publication Date Feb. 22, 2011, pp. 1-5.

Anonymous, Method and System for Enhanced Medication Management System, IP.com Prior Art Database Technical Disclosure, Publication Date Nov. 25, 2016, pp. 1-4.

Unknown, Population Health Management, Resource Guide, www.ncqa.org, content reproduced from HEDIS 2018, vol. 2: Technical Specifications for Health Plans by NCQA, 60 pages.

Smith et al., Performance Measurement for Health System Improvement: Experiences, Challenges and Prospects, Background Document, WHO European Ministerial Conference on Health Systems: "Health Systems, Health and Wealth", Tallinn, Estonia, Jun. 25-27, 2008, 28 pages.

Noy, Making it Easier to Discover Datasets, The Keyword, Google, Published Sep. 5, 2018, 3 pages.

* cited by examiner

NUTRITION-BASED MANAGEMENT OF HEALTH CONDITIONS USING MACHINE LEARNING

BACKGROUND

1. Technical Field

Present invention embodiments relate to machine learning, and more specifically, to providing nutrition-based management of health conditions using machine learning.

2. Discussion of the Related Art

Health care professionals, such as doctors, nurses, and pharmacists, deliver health care services to patients by providing treatments for diseases and symptoms of diseases. Treatments such as drugs, radiotherapy, and surgery may sometimes be risky and can have potentially serious side effects. While there are other forms of treatment that are both safe and effective, health care professionals may not be trained to provide these treatments, and patients may be unaware that such alternatives exist.

SUMMARY

According to one embodiment of the present invention, a computer system provides nutrition-based management of health conditions using machine learning. Health information of a user is evaluated to determine a health condition. Medication information for the user is analyzed and the medication information is mapped to the health condition. One or more natural treatments for the user are determined from information sources based on the mapped health condition and medication information, wherein the one or more natural treatments include one or more from a group of nutrition and mind/body treatments, and wherein the information sources include information from crowdsourcing. The one or more natural treatments and medication information for the health condition are indicated. Embodiments of the present invention further include a method and program product for providing nutrition-based management of health conditions using machine learning in substantially the same manner described above.

BRIEF DESCRIPTION OF THE DRAWINGS

Generally, like reference numerals in the various figures are utilized to designate like components.

DETAILED DESCRIPTION

Figure 1:
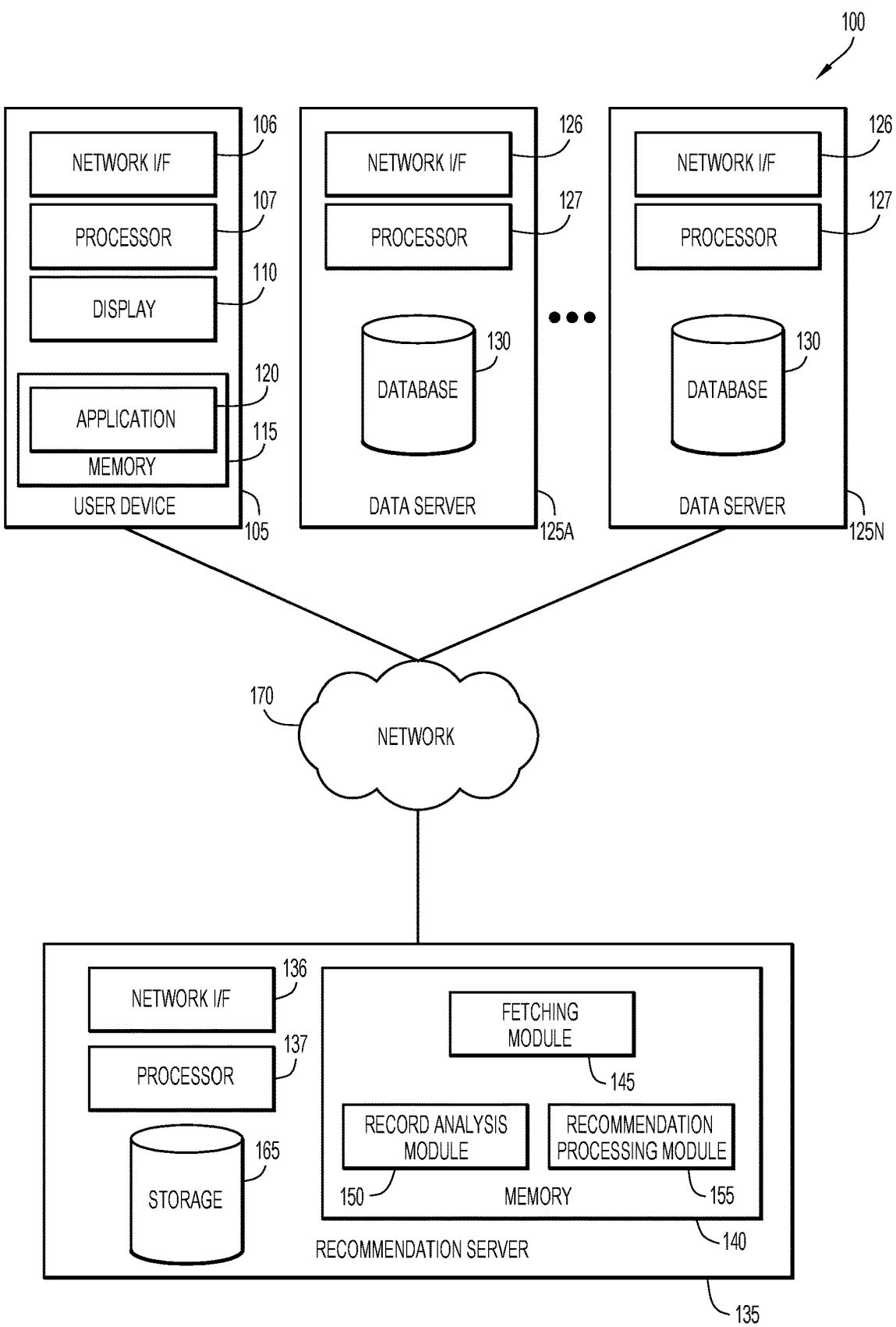
FIG. 1 is a block diagram depicting a computing environment for health condition management using machine learning in accordance with an embodiment of the present invention.

Present invention embodiments relate to natural language processing, and more specifically, to providing nutrition-based management of health conditions using natural language processing. Since conventional health care treatments may often be associated with potential risks and undesirable side effects, health conditions of users can be managed using an approach that focuses on nutrition and natural treatments. For example, a patient who is diagnosed with hypertension may be administered pravastatin, a prescription drug that lowers low density lipoprotein (LDL) cholesterol; however, pravastatin is associated with side effects that can include nausea, headaches, memory loss, and the like. However, the patient's hypertension could instead be treated by placing the patient on a specific diet and/or exercise regimen, thus addressing the patient's wellness without administering a medication that can cause side effects.

Present invention embodiments use natural language processing to provide evidence-based natural treatment options. A natural treatment can include a particular diet and/or a mind or body treatment, such as a physical activity or mental attitude. In particular, a user's electronic health records may be processed to determine a condition that the patient may have. A machine learning model that is trained with relevant health data may employ natural language processing to correlate conditions with particular treatments, which can be applied to manage a user's health condition. Furthermore, data can be collected from users who receive natural treatments in order to improve the recommendations of the machine learning model over time. Thus, present invention embodiments manage health conditions of users in a manner that addresses causes and symptoms of diseases while avoiding harmful side effects associated with other treatment options.

It should be noted that references throughout this specification to features, advantages, or similar language herein do not imply that all of the features and advantages that may be realized with the embodiments disclosed herein should be, or are in, any single embodiment of the invention. Rather, language referring to the features and advantages is understood to mean that a specific feature, advantage, or characteristic described in connection with an embodiment is included in at least one embodiment of the present invention. Thus, discussion of the features, advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages will become more fully apparent from the following drawings, description and appended claims, or may be learned by the practice of embodiments of the invention as set forth hereinafter.

Present invention embodiments will now be described in detail with reference to the Figures. FIG. 1 is a block diagram depicting a computing environment 100 for health condition management using machine learning in accordance with an embodiment of the present invention. As depicted, computing environment 100 includes a user device 105, one or more data servers 125A-125N, a recommendation server 135, and a network 170. It is to be understood that the functional division among components of computing environment 100 have been chosen for purposes of explaining present invention embodiments and is not to be construed as a limiting example.

User device 105 includes a network interface (I/F) 106, at least one processor 107, a display 110, and memory 115. Memory 115 may include application 120. User device 105 may include a laptop computer, a tablet computer, a netbook computer, a personal computer (PC), a desktop computer, a personal digital assistant (PDA), a smart phone, a thin client, or any programmable electronic device capable of executing computer readable program instructions. Network interface 106 enables components of user device 105 to send and receive data over a network, such as network 170. Users of user device 105 may include patients and/or health care professionals. User device 105 may include internal and external hardware components, as depicted and described in further detail with respect to FIG. 4.

Display 110 may include any electronic device capable of presenting information in a visual form. For example, display 110 may be a liquid crystal display (LCD), a cathode ray tube (CRT) display, a light-emitting diode (LED) display, an electronic ink display, and the like. Information relating to management of health conditions may be displayed to a user of user device 105 via display 110, including information such as health information, health condition information, natural treatment recommendations, evidence to support recommended treatments, medications for treating conditions, and the like.

Application 120 may include one or more modules or units to perform various functions of present invention embodiments described below. Application 120 may be implemented by any combination of any quantity of software and/or hardware modules or units, and may reside within memory 115 of user device 105 for execution by a processor, such as processor 107.

Application 120 may enable a user of user device 105 to input and receive data related to the management of health conditions. A user of user device 105 may input data relating to a patient's health, such as any health-related conditions, feelings, sensations, etc. that are observed by the user. A user of user device 105 may interact with application 120 in order to view treatment recommendations provided in accordance with present embodiments, including dosage amounts and other treatment details. When a user administers a treatment, the user may provide, via application 120, feedback relating to the treatment. In particular, a user may provide qualitative and/or quantitative feedback regarding the user's experiences with a treatment. For example, if a natural treatment involves a particular diet, a user may provide feedback including items that the user has consumed, times at which the user has consumed items, descriptors of symptoms or other sensations experienced by the user, and the like. Application 120 may provide an interactive management plan for a user that includes treatment options and monitoring. For example, application 120 may solicit feedback from a user over the course of the user's schedule of treatment. In some embodiments, application 120 notifies a user of user device 105 with reminders; for example, application 120 may remind a user to administer a particular substance, to perform a particular physical or mental activity, and the like. In some embodiments, application 120 may be integrated with a patient's personal information, including electronic health records of the patient. Additionally or alternatively, application 120 may integrate with one or more of a user's email account, instant messaging account, Short Message Service (SMS) client, social networking accounts, and the like.

Data servers 125A-125N each include a network interface 126, at least one processor 127, and at least one database 130. In various embodiments of the present invention, data servers 125A-125N may each include a laptop computer, a tablet computer, a netbook computer, a personal computer (PC), a desktop computer, a personal digital assistant (PDA), a smart phone, or any programmable electronic device capable of executing computer readable program instructions. Network interface 126 enables components of each data server 125A-125N to send and receive data over a network, such as network 170. In an embodiment, one or more servers of data servers 125A-125N store data relating to electronic health records of patients. Additionally or alternatively, one or more servers of data servers 125A-125N store data relating to health topics such as wellness, nutrition, medication, health conditions, and treatments for health conditions. Data servers 125A-125N may be servers that are associated with websites, such as social media websites, and/or applications, such as social media applications. Data servers 125A-125N may store data that can be accessed using conventional or other crowdsourcing techniques.

Database 130 may include any non-volatile storage media known in the art. For example, database 130 can be implemented with a tape library, optical library, one or more independent hard disk drives, or multiple hard disk drives in a redundant array of independent disks (RAID). Similarly, data on database 130 may conform to any suitable storage architecture known in the art, such as a file, a relational database, an object-oriented database, and/or one or more tables. In some embodiments, database 130 may store data relating to electronic health records of patients, and data relating to health topics such as wellness, nutrition, medication, health conditions, and treatments for health conditions.

Recommendation server 135 includes a network interface 136, at least one processor 137, memory 140, and storage 165. Memory 140 includes a fetching module 145, a record analysis module 150, and a recommendation module 155. In various embodiments of the present invention, recommendation server 135 may include a laptop computer, a tablet computer, a netbook computer, a personal computer (PC), a desktop computer, a personal digital assistant (PDA), a smart phone, or any programmable electronic device capable of executing computer readable program instructions. Network interface 136 enables components of recommendation server 135 to send and receive data over a network, such as network 170. In general, recommendation server 135 and its modules may analyze a user's health information to identify health conditions, map health conditions to medical information, determine natural treatments by applying natural language processing to information obtained from crowdsourcing, and make treatment recommendations to a user. Recommendation server 135 may include internal and external hardware components, as depicted and described in further detail with respect to FIG. 4.

Fetching module 145, record analysis module 150, and recommendation module 155 may include one or more modules or units to perform various functions of present invention embodiments described below. Fetching module 145, record analysis module 150, and recommendation module 155 may be implemented by any combination of any quantity of software and/or hardware modules or units, and may reside within memory 140 of recommendation server 135 for execution by a processor, such as processor 137.

Fetching module 145 may obtain data from one or more sources, including electronic health care records of a patient, and information that is suitable for training a machine learning model in accordance with present invention embodiments. Fetching module 145 may access a server of data servers 125A-125N in order to obtain information relating to a user, such as electronic health care records for the user. Additionally or alternatively, fetching module 145 may receive medication information for a user that identifies any medications that have been administered and/or prescribed to a patient.

Fetching module 145 may also perform conventional or other operations, such as web crawling or indexing, to crowdsource information from one or more sources, such as data servers 125A-125N. In some embodiments, data sources, such as data servers 125A-125N, may be assigned a trustworthiness score in order to rank the data sources, and fetching module 145 obtains data by crowdsourcing the data from available highly-ranked data sources (e.g., data sources whose trustworthiness scores are above a threshold level). Fetching module 145 determines a trustworthiness score for a particular data source based on feedback information that reviewers have provided regarding the data source. For example, if ninety out of one hundred reviewers indicate that a particular data source is helpful, then fetching module 145 may determine that the data source should receive a score that reflects that the data source is trustworthy. Fetching module 145 may fetch data according to a predetermined schedule or on an ad hoc basis (e.g., when new data becomes available on data servers 125A-125N).

Record analysis module 150 may analyze a user's electronic health records to identify any health conditions. In some embodiments, record analysis module 150 may analyze structured and/or unstructured health records of a patient to identify any terms, medical codes, or other identifiers that are associated with any medical condition, including physical and mental conditions. Additionally or alternatively, record analysis module 150 may analyze medication information of a patient to map each medication to a health condition of a patient based on the conditions or diseases that the medication is intended to treat. For example, if a patient is prescribed metformin, record analysis module 150 may map this medication to a type 2 diabetes condition of the patient.

Recommendation module 155 may generate recommendations of natural treatments for health conditions of patients based on the patient's health condition and medication information. In particular, recommendation module 155 utilizes a machine learning model to determine natural treatments for health conditions. The machine learning model employs natural language processing to identify associations between natural treatment options and health conditions and medications. The machine learning model may utilize any conventional or other natural language processing techniques to identify associations between natural treatments and mapped health condition and medication information. In some embodiments, the machine learning model uses a Stanford natural language processing algorithm.

The machine learning model may be trained using data obtained by fetching module 145, including information from crowdsourcing. In some embodiments, the machine learning model may place greater emphasis on data obtained from trustworthy data sources. Thus, training data obtained from data sources having higher trustworthiness scores may have a stronger influence on the model. The machine learning model may store identified associations between natural treatments and conditions in storage 165. The stored data may be tagged and/or indexed using conventional or other techniques to provide fast search return results. In some embodiments, the machine learning model also identifies amounts, dosages, or other details for each natural treatment. For example, a natural treatment recommendation may include a recommendation to consume a specified amount of a substance, such as a cup of green tea, or to perform a specified amount of a selected activity, such as jogging for one mile or meditating for twenty minutes. Recommendation module 155 may utilize conventional or other machine learning techniques, such as convolutional neural network (CNN) approaches and/or recurrent neural network (RNN) approaches, to learn associations between natural treatments and health conditions. In some embodiments, the machine learning model extracts nouns and adjectives preceding the nouns. The machine learning model may capture disease words such as "pain" or "chronic asthma," and search for anchor words such as "indication," "treatment," "relief," "reduce," and the like. Since disease words that are closer to anchor words may be more likely to be the disease treated by the drug, the machine learning model may narrow down treatment relationships between drugs and diseases.

Recommendation module 155 may generate recommendations by using a trained machine learning model to identify one or more natural treatments that are associated with a queried health condition. The queried health condition may be provided by application 120 of user device 105. Recommendation module 155 may respond with one or more natural treatments, which can be presented to a user via application 120 of user device 105. In some embodiments, recommendation module 155 may include dosage information or other details along with a recommended natural treatment.

When a user adopts a recommendation of one or more natural treatments, the user may provide follow-up feedback via application 120 of user device 105. This feedback information may be utilized by recommendation module 155 to refine the machine learning model. In particular, recommendation module 155 may perform adaptive learning to continuously adjust natural treatment recommendations in response to user feedback. Additionally or alternatively, the machine learning model may be adjusted by performing training using new data obtained by fetching module 145.

Storage 165 may include any non-volatile storage media known in the art. For example, storage 165 can be implemented with a tape library, optical library, one or more independent hard disk drives, or multiple hard disk drives in a redundant array of independent disks (RAID). Similarly, data in storage 165 may conform to any suitable storage architecture known in the art, such as a file, a relational database, an object-oriented database, and/or one or more tables. Storage 165 may store data relating to natural treatment recommendations, including mappings of medication information and conditions, natural treatments for conditions, machine learning models, crowdsourced information, feedback information, and the like.

Network 170 may include a local area network (LAN), a wide area network (WAN) such as the Internet, or a combination of the two, and includes wired, wireless, or fiber optic connections. In general, network 170 can be any combination of connections and protocols known in the art that will support communications between user device 105, data servers 125A-125N, and/or recommendation server 135 via their respective network interfaces in accordance with embodiments of the present invention.

Figure 2:
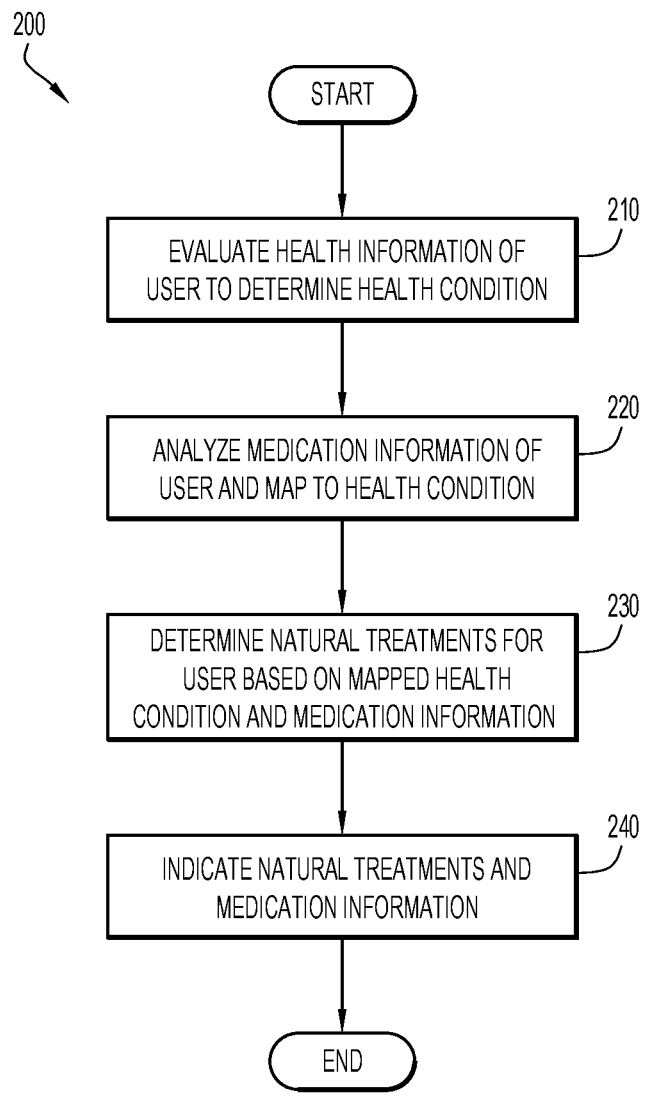
FIG. 2 is a flow chart depicting a method of managing health conditions for a patient using machine learning in accordance with an embodiment of the present invention.

FIG. 2 is a flow chart depicting a method 200 of managing health conditions for a patient in accordance with an embodiment of the present invention.

Health information of a user is evaluated to determine a health condition of the user at operation 210. Health information of a user may be obtained by fetching module 145 from a repository of electronic health record data, such as a database 130 of data servers 125A-125N. Record analysis module 150 may evaluate a user's health information to identify one or more health conditions of the user. Health conditions may include any medical condition, physical condition, mental condition, and/or combinations thereof. Record analysis module 150 may identify health conditions by processing structured and/or unstructured data to locate any terms, medical codes, or other identifiers that are associated with any health condition.

Medication information of a user is analyzed and mapped to the health condition at operation 220. Fetching module 145 may obtain medication information from a patient's electronic health records, (e.g., from a server of servers 125A-125N) or medication information may be provided by a user of user device 105, who inputs medication information of a patient via application 120. Record analysis module 150 may map the medication information to a health condition based on the medical conditions, symptoms, or diseases that the medication is intended to treat.

At operation 230, one or more natural treatments are determined for the user based on the mapped health condition and medication information. Recommendation module 155 may identify natural treatments that are related to health conditions and/or medication information by training a machine learning model using crowdsourced data. In some embodiments, the machine learning model may perform conventional or other natural language processing techniques. The crowdsourced data used for training may include data obtained from highly-ranked data sources, which may be ranked according to a trustworthiness score. Natural treatments may include nutrition options or plans, such as a particular diet, and/or mind/body natural treatments, such as physical activities and mental attitudes. For example, a natural treatment could include a dietary suggestion (e.g., a low-sodium diet), an exercise regimen (e.g., high-intensity interval training), a mindfulness technique (e.g., meditation), and the like. Natural treatments may include combinations of options; for example, a natural treatment such as tai chi may combine physical and mental treatments. Recommendation module 155 may select a natural treatment that can replace a user's medication treatment while still allowing the user to recover from a health condition.

One or more natural treatments and medication information are indicated at operation 240. Natural treatments and medication information may be presented to a user of user device 105 via application 120. In some embodiments, natural treatments and medication information are indicated during or after a user visits a health care professional, who may review the natural treatment options and discuss with the user. Natural treatments may be indicated alongside mediation information in order to present a user with an informed choice of options for treating a health condition. A recommended natural treatment may include instructions for administration of the natural treatment, such as a particular dosage amount, dosage schedule, length of time to perform a particular exercise, and the like.

In some embodiments, a user may select a presented natural treatment (e.g, via application 120 of user device 105) in order to view supporting evidence for the natural treatment. Supporting evidence may include any data upon which the machine learning model of recommendation module 155 based the recommendation. For example, if a user is presented with a natural treatment recommendation of a diet that emphasizes whole grains, lean protein, and low-fat dairy to help lower the user's blood pressure, the user may be provided with an article, medical journal publication, or other literature that contains evidence supporting this recommendation. Recommendation module 155 may send to application 120 the supporting evidence itself or a link to a location of the supporting evidence.

Figure 3:
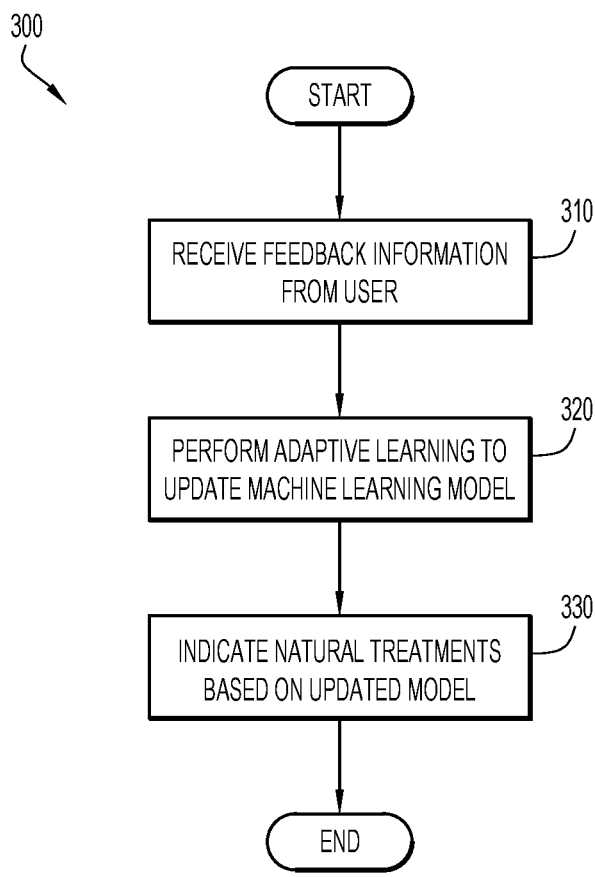
FIG. 3 is a flow chart depicting a method of adjusting a machine learning model in accordance with an embodiment of the present invention.

FIG. 3 is a flow chart depicting a method 300 of adjusting a machine learning model in accordance with an embodiment of the present invention.

Feedback information is received from one or more users at operation 310. As a user adopts a recommended natural treatment and administers the natural treatment, the user may provide feedback information to recommendation server 135 and its modules via application 120. Feedback information may include indications that a user is or is not following a recommended course of action, and any new health conditions experienced by the user, including self-reported symptoms, feelings, sensations, and the like. For example, application 120 may prompt a user to indicate whether the user has administered a natural treatment that day, and the user may provide a response or otherwise make a selection to indicate whether the user has administered the treatment. Feedback information may be received by multiple users having a variety of health conditions in order to obtain large samples of data for training purposes.

Adaptive learning is performed to update a machine learning model at operation 320. Recommendation module 155 may perform adaptive learning to continuously adjust natural treatment recommendations in response to user feedback. In particular, recommendation module 155 may perform adaptive learning by training the machine learning model using the feedback information received by users. Thus, the adaptive learning process may refine natural treatment recommendations based on previous results of users.

Natural treatments are indicated based on the updated model at operation 330. Recommendation module 155 may indicate natural treatments using the updated machine learning model that reflects user feedback. Thus, effective natural treatments may be globally up ranked for future recommendations, and ineffective natural treatments may be down ranked.

Figure 4:
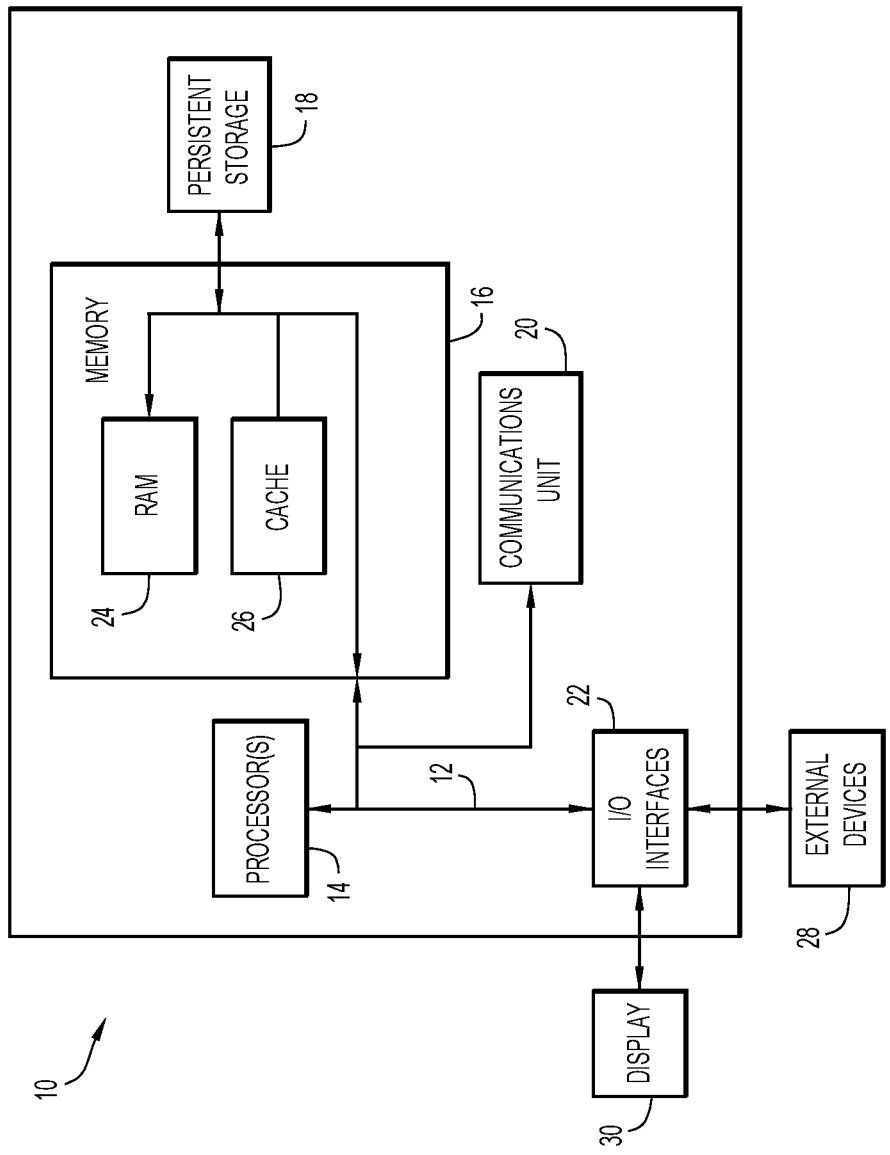
FIG. 4 is a block diagram depicting a computing device in accordance with an embodiment of the present invention.

FIG. 4 is a block diagram depicting components of a computer 10 suitable for executing the methods disclosed herein. Computer 10 may implement user devices 105, data server 125, and/or recommendation server 135 in accordance with embodiments of the present invention. It should be appreciated that FIG. 4 provides only an illustration of one embodiment and does not imply any limitations with regard to the environments in which different embodiments may be implemented. Many modifications to the depicted environment may be made.

As depicted, the computer 10 includes communications fabric 12, which provides communications between computer processor(s) 14, memory 16, persistent storage 18, communications unit 20, and input/output (I/O) interface(s) 22. Communications fabric 12 can be implemented with any architecture designed for passing data and/or control information between processors (such as microprocessors, communications and network processors, etc.), system memory, peripheral devices, and any other hardware components within a system. For example, communications fabric 12 can be implemented with one or more buses.

Memory 16 and persistent storage 18 are computer readable storage media. In the depicted embodiment, memory 16 includes random access memory (RAM) 24 and cache memory 26. In general, memory 16 can include any suitable volatile or non-volatile computer readable storage media.

One or more programs may be stored in persistent storage 18 for execution by one or more of the respective computer processors 14 via one or more memories of memory 16. The persistent storage 18 may be a magnetic hard disk drive, a solid state hard drive, a semiconductor storage device, read-only memory (ROM), erasable programmable read-only memory (EPROM), flash memory, or any other computer readable storage media that is capable of storing program instructions or digital information.

The media used by persistent storage 18 may also be removable. For example, a removable hard drive may be used for persistent storage 18. Other examples include optical and magnetic disks, thumb drives, and smart cards that are inserted into a drive for transfer onto another computer readable storage medium that is also part of persistent storage 18.

Communications unit 20, in these examples, provides for communications with other data processing systems or devices. In these examples, communications unit 20 includes one or more network interface cards. Communications unit 20 may provide communications through the use of either or both physical and wireless communications links.

I/O interface(s) 22 allows for input and output of data with other devices that may be connected to computer 10. For example, I/O interface 22 may provide a connection to external devices 28 such as a keyboard, keypad, a touch screen, and/or some other suitable input device. External devices 28 can also include portable computer readable storage media such as, for example, thumb drives, portable optical or magnetic disks, and memory cards.

Software and data used to practice embodiments of the present invention can be stored on such portable computer readable storage media and can be loaded onto persistent storage 18 via I/O interface(s) 22. I/O interface(s) 22 may also connect to a display 30. Display 30 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Data relating to nutrition-based management of health conditions (e.g., natural treatment information, medication information and condition mapping information, machine learning model information, crowdsourced information, feedback information, etc.) may be stored within any conventional or other data structures (e.g., files, arrays, lists, stacks, queues, records, etc.) and may be stored in any desired storage unit (e.g., database, data or other repositories, queue, etc.). The data transmitted between user device 105, data servers 125A-125N, and/or recommendation server 135 may include any desired format and arrangement, and may include any quantity of any types of fields of any size to store the data. The definition and data model for any datasets may indicate the overall structure in any desired fashion (e.g., computer-related languages, graphical representation, listing, etc.).

Data relating to nutrition-based management of health conditions (e.g., natural treatment information, medication information and condition mapping information, machine learning model information, crowdsourced information, feedback information, etc.) may include any information provided to, or generated by, user device 105, data servers 125A-125N, and/or recommendation server 135. Data relating to nutrition-based management of health conditions may include any desired format and arrangement, and may include any quantity of any types of fields of any size to store any desired data. The data relating to nutrition-based management of health conditions may include any data collected about entities by any collection mechanism, any combination of collected information, and any information derived from analyzing collected information.

The present invention embodiments may employ any number of any type of user interface (e.g., Graphical User Interface (GUI), command-line, prompt, etc.) for obtaining or providing information (e.g., data relating to nutrition-based management of health conditions), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

It will be appreciated that the embodiments described above and illustrated in the drawings represent only a few of the many ways of providing nutrition-based management of health conditions using machine learning.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, application 120, fetching module 145, record analysis module 150, recommendation module 155, etc.). These systems may include any types of monitors and input devices (e.g., keyboard, mouse, voice recognition, etc.) to enter and/or view information.

It is to be understood that the software (e.g., browser software, communications software, server software, application 120, fetching module 145, training module 150, natural language processing module 155, etc.) of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments (e.g., browser software, communications software, server software, application 120, fetching module 145, record analysis module 150, recommendation module 155, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., data relating to nutrition-based management of health conditions). The database system may be implemented by any number of any conventional or other databases, data stores or storage structures (e.g., files, databases, data structures, data or other repositories, etc.) to store information (e.g., data relating to nutrition-based management of health conditions). The database system may be included within or coupled to the server and/or client systems. The database systems and/or storage structures may be remote from or local to the computer or other processing systems, and may store any desired data (e.g., data relating to natural language processing using an ontology-based concept embedding model).

The present invention embodiments may employ any number of any type of user interface (e.g., Graphical User Interface (GUI), command-line, prompt, etc.) for obtaining or providing information (e.g., data relating to nutrition-based management of health conditions), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The present invention embodiments are not limited to the specific tasks or algorithms described above, but may be utilized for any number of applications in the relevant fields, including, but not limited to, applying natural language processing and machine learning toward the management of health conditions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method for providing nutrition-based management of health conditions, the computer-implemented method comprising:
    evaluating, via a processor, health information of a user to determine a health condition;
    analyzing, via the processor, medication information for the user and mapping the medication information to the health condition;
    determining, via the processor, trustworthiness scores for a plurality of information sources based on feedback information that reviewers have provided regarding the information sources;
    crowdsourcing information from the information sources based on the trustworthiness scores, via the processor, and determining one or more natural treatments for the user based on the mapped health condition and medication information, wherein the one or more natural treatments include one or more from a group of nutrition and mind/body treatments, and wherein determining the one or more natural treatments further comprises:
        training, via the processor, a machine learning model with the information from crowdsourcing to learn natural treatments for health conditions, wherein the information from crowdsourcing information sources with a trustworthiness score above a threshold level have greater influence on the training of the machine learning model; and applying, via the processor, the health condition and medication information to the machine learning model to determine the one or more natural treatments for the health condition;

indicating, via the processor, the one or more natural treatments and medication information for the health condition;

monitoring, via the processor, the health condition of the user in response to administration of the one or more natural treatments; and updating, via the processor, the machine learning model by performing machine learning based on the monitoring, wherein the machine learning model provides future recommendations of one or more natural treatments based on the updating.

2. The computer-implemented method of claim 1, wherein indicating the one or more natural treatments further comprises:

indicating, via the processor, the one or more natural treatments with one or more corresponding information sources providing evidence for the one or more natural treatments.

3. The computer-implemented method of claim 1, wherein indicating the one or more natural treatments further comprises:

indicating, via the processor, the one or more natural treatments with corresponding amount information and a monitoring plan.

4. The computer-implemented method of claim 1, wherein a natural treatment of nutrition includes a diet providing one or more foods to consume, and a mind/body natural treatment includes one or more from a group of physical activities and mental attitude.

5. The computer-implemented method of claim 1, wherein the health condition includes one or more from a group of medical conditions, physical conditions, and mental conditions.

6. A computer system for providing nutrition-based management of health conditions, the computer system comprising:

one or more computer processors;

one or more computer readable storage media;

program instructions stored on the one or more computer readable storage media for execution by at least one of the one or more computer processors, the program instructions comprising instructions to:

evaluate health information of a user to determine a health condition;

analyze medication information for the user and map the medication information to the health condition;

determine trustworthiness scores for a plurality of information sources based on feedback information that reviewers have provided regarding the information sources;

crowdsource information from the information sources based on the trustworthiness scores and determine one or more natural treatments for the user based on the mapped health condition and medication information, wherein the one or more natural treatments include one or more from a group of nutrition and mind/body treatments, and wherein determining the one or more natural treatments further comprises:

training a machine learning model with the information from crowdsourcing to learn natural treatments for health conditions, wherein the information from crowdsourcing information sources with a trustworthiness score above a threshold level have greater influence on the training of the machine learning model; and applying the health condition and medication information to the machine learning model to determine the one or more natural treatments for the health condition;

indicate the one or more natural treatments and medication information for the health condition;

monitor the health condition of the user in response to administration of the one or more natural treatments; and update the machine learning model by performing machine learning based on the monitoring, wherein the machine learning model provides future recommendations of one or more natural treatments based on the updating.

7. The computer system of claim 6, wherein the instructions to indicate the one or more natural treatments further comprise instructions to:

indicate the one or more natural treatments with one or more corresponding information sources providing evidence for the one or more natural treatments.

8. The computer system of claim 6, wherein the instructions to indicate the one or more natural treatments further comprise instructions to:

indicate the one or more natural treatments with corresponding amount information and a monitoring plan.

9. The computer system of claim 6, wherein a natural treatment of nutrition includes a diet providing one or more foods to consume, and a mind/body natural treatment includes one or more from a group of physical activities and mental attitude.

10. The computer system of claim 6, wherein the health condition includes one or more from a group of medical conditions, physical conditions, and mental conditions.

11. A computer program product for providing nutrition-based management of health conditions, the computer program product comprising one or more computer readable storage media collectively having program instructions embodied therewith, the program instructions executable by a computer to cause the computer to:

evaluate health information of a user to determine a health condition;

analyze medication information for the user and map the medication information to the health condition;

determine trustworthiness scores for a plurality of information sources based on feedback information that reviewers have provided regarding the information sources;

crowdsource information from the information sources based on the trustworthiness scores and determine one or more natural treatments for the user based on the mapped health condition and medication information, wherein the one or more natural treatments include one or more from a group of nutrition and mind/body treatments, and wherein determining the one or more natural treatments further comprises:

training a machine learning model with the information from crowdsourcing to learn natural treatments for health conditions, wherein the information from crowdsourcing information sources with a trustworthiness score above a threshold level have greater influence on the training of the machine learning model; and applying the health condition and medication information to the machine learning model to determine the one or more natural treatments for the health condition;

indicate the one or more natural treatments and medication information for the health condition;

monitor the health condition of the user in response to administration of the one or more natural treatments; and update the machine learning model by performing machine learning based on the monitoring, wherein the machine learning model provides future recommendations of one or more natural treatments based on the updating.

12. The computer program product of claim 11, wherein the program instructions to indicate the one or more natural treatments further cause the computer to:

indicate the one or more natural treatments with one or more corresponding information sources providing evidence for the one or more natural treatments.

13. The computer program product of claim 11, wherein the program instructions to indicate the one or more natural treatments further cause the computer to:

indicate the one or more natural treatments with corresponding amount information and a monitoring plan.

14. The computer program product of claim 11, wherein a natural treatment of nutrition includes a diet providing one or more foods to consume, and a mind/body natural treatment includes one or more from a group of physical activities and mental attitude.

15. The computer program product of claim 11, wherein the health condition includes one or more from a group of medical conditions, physical conditions, and mental conditions.

* * * * *